United States Patent [19]

Stanley et al.

[11] 4,073,294
[45] Feb. 14, 1978

[54] NEGATIVE PRESSURE DRAINAGE VESSEL

[75] Inventors: James Robert Stanley; Silas Charles Topham, both of Orem, Utah

[73] Assignee: Medical Development Corporation, Salt Lake City, Utah

[21] Appl. No.: 598,369

[22] Filed: July 23, 1975

[51] Int. Cl.$^2$ ............................................. A61M 1/00
[52] U.S. Cl. ............................................. 128/278
[58] Field of Search ............................ 128/276–278, 128/297–300; 417/395, 472, 479

[56] References Cited

U.S. PATENT DOCUMENTS

| 2,890,699 | 6/1959 | Miller | 128/278 |
| 3,111,145 | 11/1963 | Kerns | 128/278 |
| 3,809,086 | 5/1974 | Schachet et al. | 128/278 |
| 3,889,677 | 6/1975 | Nehring | 128/278 |

*Primary Examiner*—Dalton L. Truluck
*Assistant Examiner*—Henry S. Layton
*Attorney, Agent, or Firm*—Fitch, Even, Tabin & Luedeka

[57] ABSTRACT

A negative pressure drainage vessel equipped with an interior resilient flexible diaphragm and means for producing a negative pressure on that side of such diaphragm which is proximate a fluid recovery area. The opposite side of the diaphragm is exposed to atmospheric pressure. A progressive rise of fluid level in the container, as may tend to increase the pressure on the negative-pressure side of the diaphragm, is accompanied by an elastomeric contraction "pull-down" or "pull-up" of the diaphragm so as to maintain essentially the negative pressure required for an essentially constant suction condition for a large progressive rise in fluid level. The negative pressure may be increased by periodic application of vacuum as may be effected by an air-evacuation mechanism. A separate, liquid-filled bag may be employed together with an appropriate valving means.

7 Claims, 21 Drawing Figures

NEGATIVE PRESSURE DRAINAGE VESSEL

The present invention relates to negative pressure vessels for recovering fluids and, more particularly, to a new and improved aspiration vessel having a negative-pressure stabilizing diaphragm.

In the past, a number of types of vessels have been designed for aspiration purposes. Specialized equipment is also available on the market for fluid drainage purposes in the medical arts. It is frequently desirable to drain body fluids from a hospital patient, for example, in a manner as to accelerate slightly normal gravity or other flow. Frequently, negative-pressure vacuum must be used to draw objectionable fluids from the bladder, abdomen, limbs, or other body areas. While vacuum pumps can be used, frequently this becomes inconvenient since a patient may be ambulatory, or perhaps the patient, if in the field, may not have access to electrically-powered vacuum equipment.

In the present invention a squeeze bulb and resilient diaphragm are used, with certain valving structure as a non-machine-type means for producing a negative pressure in the nature of a constant mild suction within an aspiration vessel. The vessel itself is provided with an inside diaphragm, one side of which is exposed to the outside atmosphere as through container holes. Upon evacuating the vessel region on the opposite side of the diaphragm, atmospheric pressure is relied upon to distend, i.e. extend the diaphragm within the evacuation chamber. As fluid is progressively drawn into such chamber, the fluid will displace the negative pressure gaseous area so as to tend to increase positively, slightly, such negative pressure of that area. The diaphragm, however, in specifically being chosen to be elastomeric and resilient, tends to move in a direction toward its original, essentially flat configuration, so as to tend to preserve the negative pressure character of the evacuation area of the vessel, thereby facilitating a continuation of required, negative-pressure aspiration of incoming fluids. The reduced air-pressure or vacuum at the negative pressure area may be progressively further reduced during or between aspiration uses, by manual, vacuum pumping means. Preferably, liquid measure and vacuum measurement index lines are provided the translucent container so that least approximate measurements relative to vacuum and contents may be made at any time. Suitable drain means as well as fluid inlet means are provided. Optionally, a liquid-fill bag with appropriate valving is supplied, and diaphragm extension is reversed.

Accordingly, a principal object of the present invention is to provide a new and improved negative pressure aspiration vessel.

A further object is to provide a negative pressure vessel for collecting aspirated fluids, wherein such vessel is provided with hand-operated, vacuum-producing means.

An additional object is to provide a negative pressure vessel having a diaphragm exposed to atmospheric pressure and capable of being distorted or extended to protrude into the vacuum region of the vessel, with the resiliency of the diaphragm being relied upon to gradually return the diaphragm back to its initial condition, upon a progressive fluid rise, and thereby tend to maintain the necessary negative pressure proximate such fluid to facilitate continued fluid recovery.

A further object is to provide a new and improved diaphragm including aspiration vessel which is conveniently operated by hand pump means to produce negative pressure desired for effective aspiration in such vessel.

The features of the present invention which are believed to be novel are set forth with particularity in the appended claims. The present invention, both as to its organization and manner of operation, together with further objects and advantages thereof, may best be understood by reference to the following description, taken in connection with the accompanying drawings, in which:

FIGS. 5A and 5B are longitudinal, horizontal sections of certain, manually-actuated exhaust apparatus utilized with the vessel in evacuating a region thereof on one side of the diaphragm employed. FIG. 5A illustrates air as being exhausted from the squeeze bulb structure shown, and FIG. 5B illustrates air as being drawn from the chamber to the squeeze bulb area.

FIG. 6A is a side elevation of the aspiration vessel of the invention and is cut away to illustrate the diaphragm employed in its usual condition, i.e. when a negative pressure is not applied to the vessel.

FIG. 6B is a view similar to FIG. 6A but illustrates the negative pressure as having been produced by the structure of FIGS. 5A and 5B, so as to cause a distortion of the diaphragm toward the incoming fluid level.

FIG. 6C is similar to FIG. 6B but illustrates a progression of the diaphragm, though the same is spaced from its rising fluid level, as progressively more fluid is drawn into the vessel, such action serving to preserve essentially and maintain the negative pressure condition of that side of the diaphragm proximate the fluid level.

FIG. 6D is similar to FIG. 6C, but illustrates further negative pressure in the sense of new or increased vacuum being applied via the squeeze bulb structure of FIGS. 5A and 5B, for extending downwardly the diaphragm to thereby effect an increased negative pressure effect and suction of the device, and this whether the chamber is partially full or empty.

FIG. 7 is an enlarged, fragmentary view taken along the arrow 7 in FIG. 2, showing the index of lines that can be employed on the side walls of the vessel to indicate liquid measure and also vacuum measure for the amount of vacuum being applied at that level.

FIG. 8 is an exploded view of one form of aspiration vessel herein when elevated with respect to its pouch.

Figure 1:
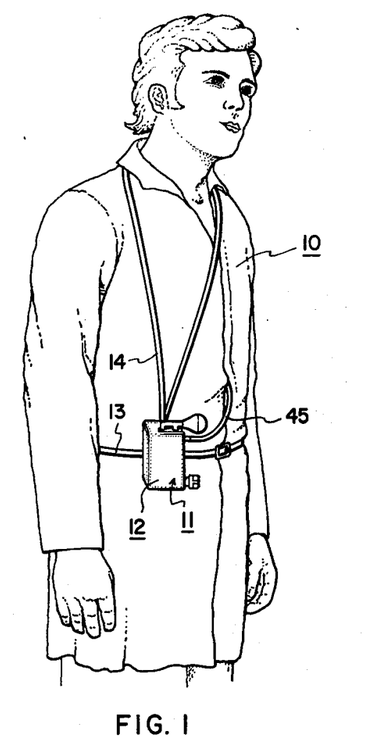
FIG. 1 is a perspective view of a hospital patient wearing the aspiration vessel, to effect body fluid drainage.

In FIG. 1, a patient 10 is shown wearing the body fluid drainage vessel 11 by means of a pouch 12 which is provided with belt 13 and strap 14.

Figure 5A:
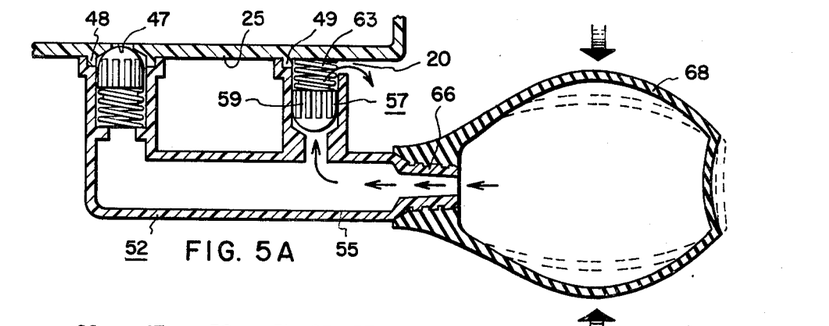
Figures 5B, 6A, 6B, 6C, 6D, 7, 8:
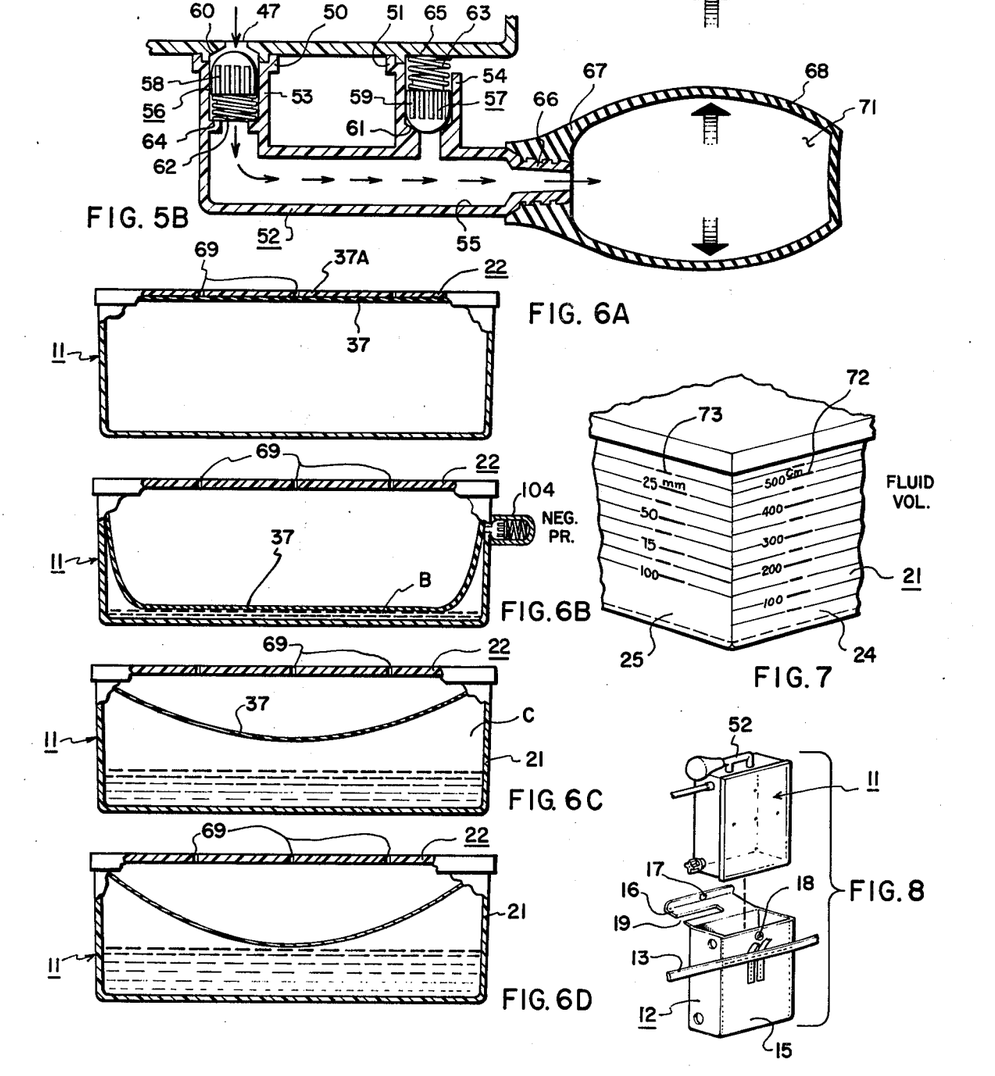
Figure 9:
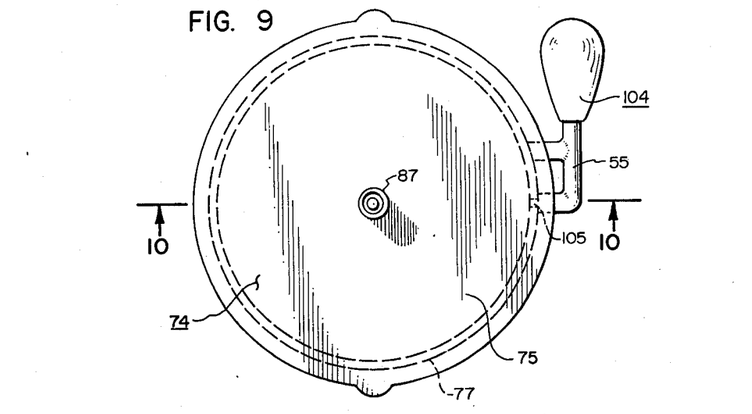
FIG. 9 is a top plan of an aspiration container in another embodiment of the invention.

More specifically, FIG. 8 illustrates the vessel 11 as releasable from pouch 12 in the manner indicated. Thus, pouch 12 may include a pocket member 15 provided with lid 16 having snap fasteners 17. Fastener 18 is provided to cooperate therewith. The lid 16 will include a slot 19 accommodating the conduit member 52 of vessel 11.

Figure 2:
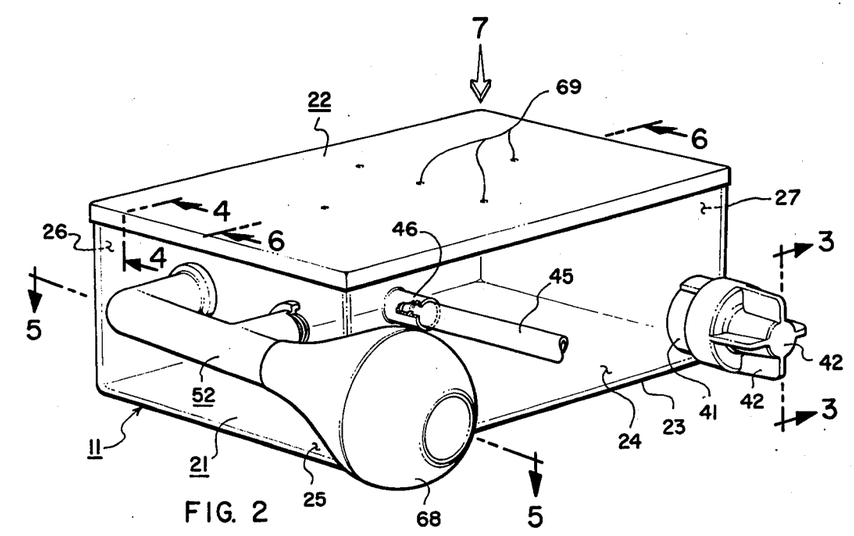
FIG. 2 is a perspective view of the aspiration vessel of the invention when the same is disposed or placed on a horizontal support plane.

In turning to FIG. 2 it is seen that the vessel 11 comprises a container 21 and a cover 22 secured therto in a sealing engagement.

Figure 4:
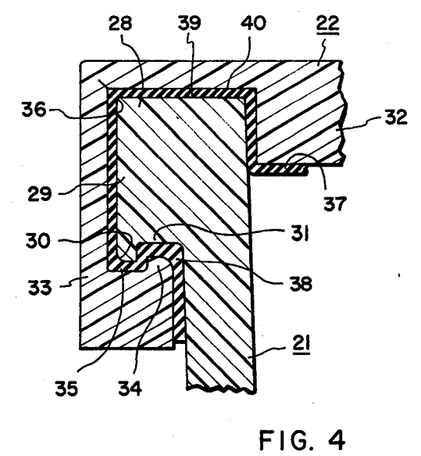
FIG. 4 is an enlarged fragmentary section, taken along the line 4—4 in FIG. 2, of a representative top corner lip of the structure.

Container 21 has a bottom 23 and side portions 24-27. The peripheral lip 28 of container 21 has a transverse cross-section as shown in FIG. 4. The same is seen to include an upper, outwardly enlarged margin 29 that is provided with rib portion 30 and elongate groove 31.

For cooperative engagement with container 21, cover 22 is provided with a central portion 32 and also a peripheral flange 33. See again FIG. 4 wherein the flange 33 is shown to include an inner tongue 34 and also a contiguous groove 35. The cover may be made of a slightly flexible, plastic material, this so that the peripheral flange 33 may be disposed outwardly over edge 36 of container lip 28 as the cover 22 is snapped over margin 29 to achieve the engagement shown in FIG. 4.

A sheet-like or molded elastomeric material is provided to form a diaphragm 37 that has a peripheral margin 38 disposed between adjacent surfaces 39 and 40 of the container 21 and cover 22, respectively. Thus, the diaphragm aids in the sealing function as to cover 22 relative to container 21, and, additionally, is slightly stretched so that the same will achieve a flat horizontal configuration as shown at 37 in FIG. 4.

It is to be noted that the thickness and stretch of the diaphragm, in all embodiments of the invention, will determine, in conjunction with the operation of the squeeze bulb, the vacuum level of the container.

Figure 3:
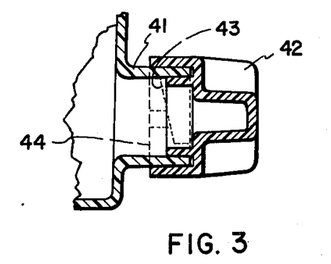
FIG. 3 is an enlarged section taken along line 3—3 in FIG. 2, illustrating one representative drainage structure for such vessel.

The container 21 proximate bottom 23 is provided with a drain port 41, configured in the usual manner and provided with a manually rotatable drain plug 42. The two inter-cooperate in a conventional fashion as shown in FIG. 3, with lug camming surfaces at 43 and lugs 44 being provided to establish a secure, sealed fit as between the drain plug 42 and the port 41 when the former is releasably installed over such port. Fluid inlet conduit 45 is secured to inlet port 46. Preferably, the latter will include an internal, annular transverse rib for releasably frictionally retaining the fluid inlet conduit 45 in the manner shown in FIG. 2. Optionally, conduit 45 can be welded in place to prevent the possibility of cross-contamination to the patient and also leaking from the patient at this point.

The side 25 of container 21 includes apertures 47 and exterior annular ring portions 48 and 49, see FIGS. 5A-5B, which serve as mounts for receiving the receiver mounts 50 and 51 of conduit member or casing 52. Conduit member 52 thus includes passageway portions 53 and 54 which are contiguous with passageway portion 55. Portions 53 and 54 are individually provided with an air intake valve 56 and also an air exhaust valve 57. These take the form of valve gates 58 and 59 which work against respective valve seats 60 and 61. The valves are backed by compression springs 62 and 63, and these react against shoulder 64 and surface 65.

Conduit member 52 is provided with a nipple 66 that receives an exterior receiver portion 67 of squeeze bulb 68. It is noted in FIG. 2 that aperture 47 is disposed underneath the diaphragm 37 of FIG. 4. Accordingly, the squeeze bulb operates to evacuate air from underneath the diaphragm with respect to FIGS. 2-4.

The appratus as thus far described operates as follows:

At the outset, drain line or conduit 45 will communicate with the interior of the patient and will be sutured or otherwise secured in place as the same extends out of the body and connects to port 46. Aspiration vessel 11 is preliminarily introduced into pouch 12 and is secured by belt 13 and strap 14 in a comfortable position at the side of the patient. Drain plug 42, of course, will be installed in place and closed.

Optionally, the unit can be positioned on a horizontal surface such as at the patient's bedside, near his bed or on a stand, and be disposed in the manner shown in FIG. 2. It should be understood that the device can be oriented in any manner desired, the discussion which follows will assume the vessel is oriented in the manner shown in FIGS. 2 and 6A-6D.

At the outset it is to be noted that diaphragm 37 always receives atmospheric pressure at its upper surface 37A, by virtue of the fact that the cover 22 will include a series of atmospheric-air communicating apertures 69. Accordingly, squeeze bulb 68 will be intermittently squeezed and released so as to evacuate air from underneath diaphragm 37. The manner in which this is accomplished is as follows. First, the squeeze bulb 68 is squeezed so that the air is forced outwardly in the direction of the arrows shown in FIG. 5A, through valve 57. This action thus serves to expel air from squeeze bulb 68 through aperture 20.

When hand pressure is released from the bulb, see the condition shown in FIG. 5B, then squeeze bulb 68 expands so as to draw into the bulb area air from that portion of container 21 which is beneath diaphragm 37. This serves to progressively pull or expand the diaphragm downwardly in the direction shown in FIG. 6B so that the same "grows" downwardly in this embodiment, resulting in a production of a mild negative pressure area beneath the diaphragm to enable the container to draw in fluid through conduit 45.

As the fluid level continues to rise, see the progression from FIG. 6B to FIG. 6C, then the density of any remaining gaseous media, such as air, beneath diaphragm 37 will increase, owing to the current volumetric presence of incoming fluid beneath the diaphragm, thus reducing the pressure differential on opposite sides of diaphragm 37. This action initiates a tendency of the diaphragm to contract; more importantly, however, the progressively contracting diaphragm draws fluid from the patient inwardly toward the container and upward with the container, toward and against the underside of the diaphragm. Specifically, continued rises, or contraction of the diaphragm operates in effect as a suction-plunger during its retrieval, so that the major portion of the vacuum space beneath the diaphragm is filled, by replacement, with the incoming rising fluid. This action permits the diaphragm to continue its contraction, so as to "suck in" or draw in yet further fluid, and this over a prolonged, essentially mild-vacuum condition until the diaphragm at last reaches its upper, horizontal, rest position. Accordingly, the aspiration function continues to persist and is effective to draw in a greater amount of fluid than that recoverable were the diaphragm absent. Of course, a further minus increase in negative pressure can be developed at any time through further actuation of the squeeze bulb 68 so that the diaphragm distends downwardly to the position shown in FIG. 6D, hence enlarging negative pressure proximate the fluid level.

The negative pressure and fluid volume index lines seen in FIG. 7, when used, will aid in ascertaining both liquid and relative vacuum measurements, and permits the setting of desired vacuum limits.

To emphasize, it is seen that by virtue of the tendency of the diaphragm to want to assume its original condition as shown in FIG. 6A, that the suction effect through gradual contraction of the diaphragm and the vacuum-area fluid-replacement phenomenon above described, will tend to be maintained at area C even though level of fluid received by the container tends to rise. The automatic self-adjustment of the structure, caused by the progressive rise of the diaphragm, will operate to increase the ability of the container to draw in fluid under a sustained effective negative pressure condition sustained at the diaphragm as the same is in process of contracting. Of course, if the patient or medical attendant wishes to increase the level of negative pressure in the container at any particular time, then the squeeze bulb 68 need only be actuated as aforesaid in order to increase the "pull-down" of the resilient diaphragm through the atmospheric pressure, vacuum pressure differential across the diaphragm enabling the diaphragm to rise upwardly as additional fluid is drawn into the cavity.

In fabrication, any suitable rigid plastic material, preferably either transparent or translucent, may be used for molding container 21. Cover 22, having a molded peripheral flange, will preferably be fabricated from high density polyethylene. An elastomeric material such as latex rubber having a thickness of 0.010 inches, by way of example, will be suitable for diaphragm 37. This can be varied, with planar tension or "stretch".

Special notice is to be taken of the fact that to accomodate the various vacuum ranges that may be required, the diaphragm provides means not only for enabling the application of negative pressure above the incoming aspirated fluid, but also essentially maintains such mild negative pressure condition as the fluid rises to displace the vacuum there beneath.

The diaphragm, when distended as shown in FIG. 6C, may be designed to be used to automatically seal off aperture 47 in FIG. 5B, to preclude any possibility of fluid presence at or leakage past valve 58. Bulb 68 can be shortened, if desired, so as not to protrude past container side 24 in FIG. 2.

FIGS. 9-12 illustrate another embodiment of the invention, wherein aspiration vessel 74 includes a cover 75, a base 76, and a container cylinder 77. Base 76 and cylinder 77 comprise a container 78. Disposed between base 76 and the cylinder 77 is the outer peripheral margin 79 of an expandable diaphragm 80. For securement purposes the container cylinder 77 may include an outwardly extending bead 81 which presses diaphragm margin 79 into the recessed area 82 of base flange 83. A corresponding configuration may exist at the top of the container cylinder 77 so that the latter will be provided with a peripheral sealing lip 84 that fits into groove 85, the latter being associated with annular flange 86 of cover 75.

Figure 10:
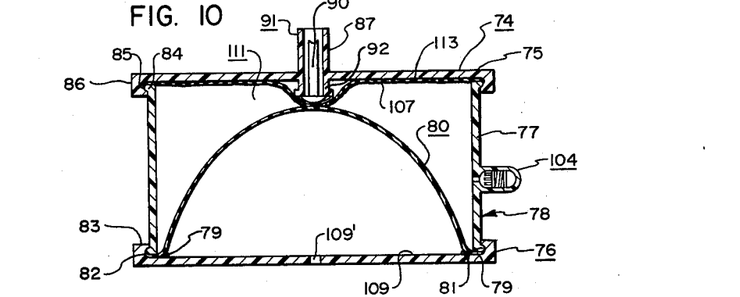
FIG. 10 is a transverse vertical section as taken along the line 10—10 in FIG. 9.
Figure 10A:
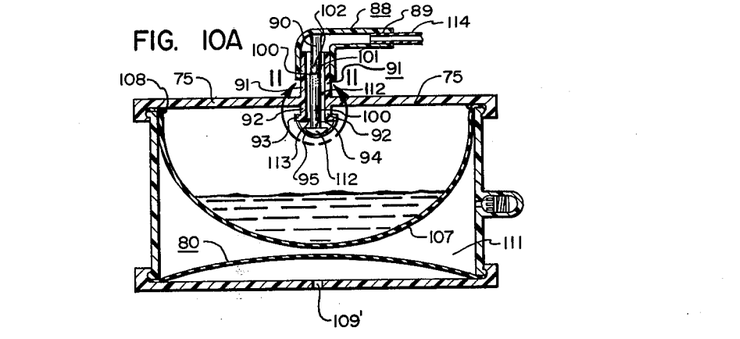
FIG. 10A is similar to FIG. 10, but illustrates the fluid-fill bag as being downwardly expanded.
Figure 11:
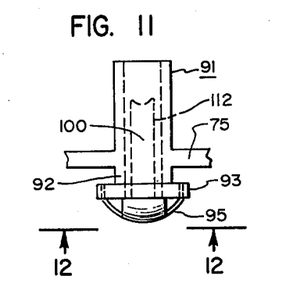
FIG. 11 is an enlarged fragmentary detail taken along the arcuate line 11—11 in FIG. 10A.
Figure 12:
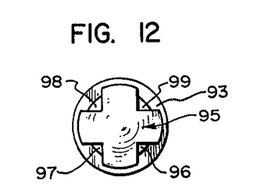
FIG. 12 is a bottom plan taken along the line 12—12 in FIG. 11.

A hollow boss 87 takes the form of the patient port 91 and is constructed to receive port fitting 88 as shown in FIG. 10A. The latter includes a Leur opening 89, is L-configured, and includes a central push-rod finger 90. Port 91, associated with boss 87, includes a depending portion 92 which mounts ring 93, which mounts elastomeric, resilient diaphragm valve 95.

Ring 93, cemented to portion 92, includes the elastomeric expandable end or valve 95 that is provided with a series of open corners at 96-99 which close against the combination of ring 93 and port end 94. A plunger 100 acts against such diaphragm and includes socket 101 receiving the rounded end 102 of push-rod finger 90. Evacuation pumping unit 104 may take the identical form of the entire structure shown in FIGS. 5A and 5B; thus, the container cylinder 77 will include port 105 which will correspond to port 47 in FIG. 5B. Of importance is the inclusion of collector bag 107, the same being heat-seamed or otherwise secured, as by an epoxy cement at 108, to cover 75.

The structure shown in FIGS. 9-12 operates as follows: At the outset, of course, the diaphragm 80 will be collapsed toward the bottom of the container, i.e. at the upper surface 109 of base 76. Space 111, which is disposed between diaphragm 80 and cover 75, is closed.

An aperture 109' is provided at base 76 so as to provide atmospheric pressure on the underside of diaphragm 80. Accordingly, such diaphragm, by virtue of ambient air pressure, will proceed upwardly to the condition shown in FIG. 10 when air is pumped out of space 111 by hand pumping unit 104.

The operation of valve 95 will now be discussed. It is noted that ring 93 is provided with expandable, resilient, elastomeric valve element or cross 95, the same having the openings or corners 96-99 which offer communication through anular passageway 112 to the opening at 89 in FIG. 10A. This occurs, however, only when the plunger 100 is depressed by push-rod or finger 102. The elastomeric valve 95, by its resiliency, will push upwardly the plunger 100 in the absence of downward pressure of push-rod 90, so that enlarged end 112 will seal off aperture 113 in FIG. 10A.

The dimension and resiliency of bag 107 will be such, see FIG. 10, that the same is proximate of the under-surface 113 of cover 75 in the absence of vacuum pressure being applied. The patient tube 114 is now installed and ready for usage. The user will actuate the bulb provided vacuum producing unit 104 so as to withdraw air from space 111 in FIG. 10. This causes an upward rise in diaphragm 80 as produced by atmospheric air entering aperture 109.

The negative pressure condition in space 111 will depress downwardly slightly the bag 107; and depression of push-rod 90, so as to open plunger 100 to expose aperture 94, will cause a flowing in of fluid by virtue of this initial vacuum produced within bag 107. The way to the incoming fluid aids in a progressive expansion downwardly of the bag 107, which further serves to increase the drawing effect upon patient fluid and its flow through opening 113. The fluid level will hence gradually rise in the bag, and as more space within space 111 is taken up by the expanding bag, the negative pressure with space 111 will lessen so as to reduce the expansion of diaphragm 80. See FIG. 10A.

When the fitting 88 is pulled upwardly, then the connection to the patient is effectively blocked and the patient tube can be removed. Where desired, the cover 75 can simply be snapped off its position and the unit thrown away with the bag 107 being filled, or essentially so.

What is provided, therefore, is a unit having an independent bag which can be progressively filled by patient fluid with the operation of a vacuum. When the lid is removed, the same can be replaced by a new unit, and, since base 111 will now be again at atmospheric pressure, the procedure can be repeated.

Figure 13:
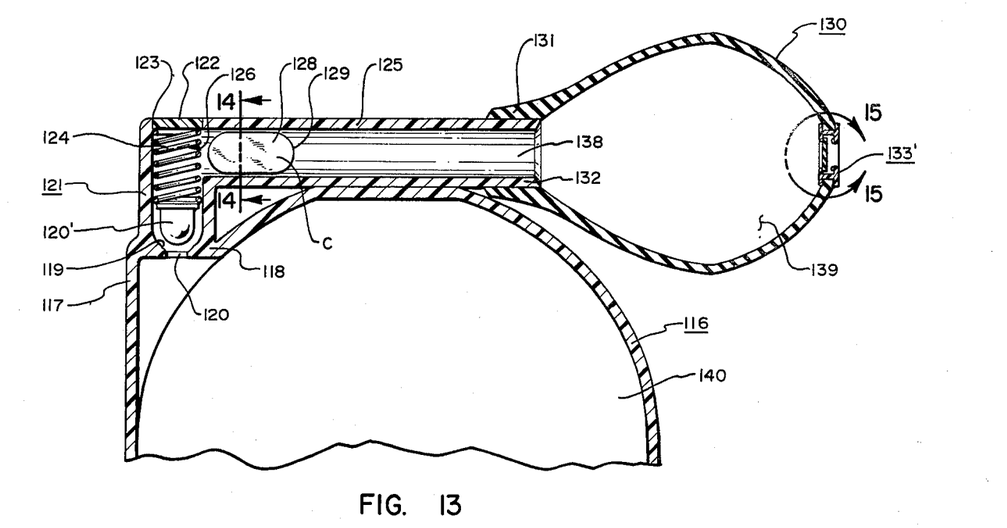
FIG. 13 is a fragmentary top plan, shown principally in section, of an alternate form of the invention incorporating a different type of squeeze bulb construction.
Figure 14:
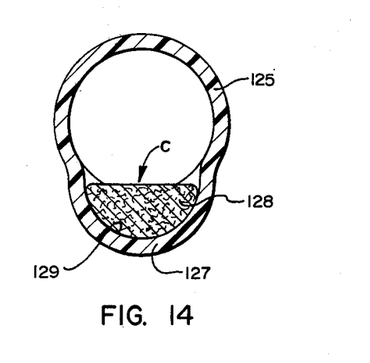
FIG. 14 is an enlarged fragmentary cross-section taken along the line 13—13 in FIG. 13, illustrating a moisture trap.

In FIG. 13 a container 116 corresponds to a container such as at 78 in FIG. 10, but this time is shown to be arcuate in shape. For convenience of illustration the lid or cover is shown removed; however, it may consist of any one of the several covers or lids shown in prior embodiments as at 32 in FIG. 4 and 22 in FIG. 6A.

In any event, the container 116 will be provided with a container extension 117 provided with a partition 118, the same being provided a valve seat 119 encompassing aperture 120. Structure 121 is integral with or otherwise secured to the container and includes plug 122 when secured in opening 123, backs a compression-type return spring 124 as shown. Conduit 125 communicates with the open interior 126 of structure 121 and is provided with a depending, bubble-like lateral extension 127 that forms a lateral chamber receiving moisture-absorbent cotton wad 128. The depression 129 of chamber C in which the cotton or other absorbent material is placed, will catch any fluid mist that might be present and which should not be transmitted to and through the squeeze bulb area.

Figure 15:
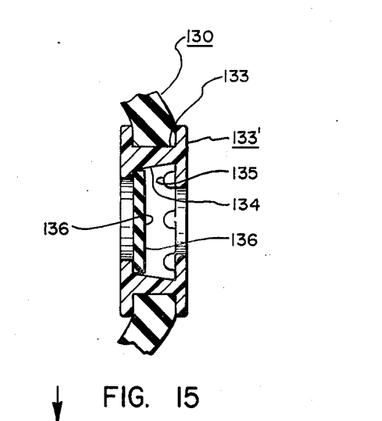
FIG. 15 is an enlarged detail taken along the line 15—15 in FIG. 13, this figure illustrating a closed valve condition.
Figure 16:
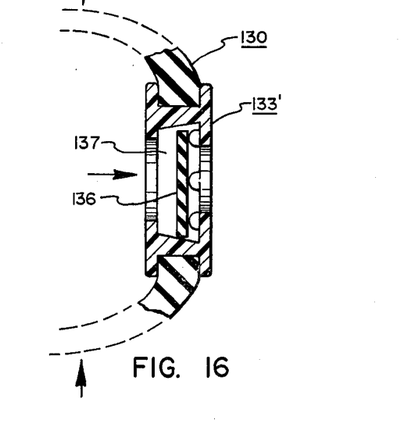
FIG. 16 is similar to FIG. 15, but illustrates that when hand pressure is applied to the squeeze bulb to squeeze the same, the valve at the extremity of the squeeze bulb opens for the purpose of exhausting air from the squeeze bulb.

Squeeze bulb 130, is affixed at its neck 131 to extremity 132 of conduit 125 and is provided with an open end at 133. End 133 includes an eye 133' which is shown in detail in FIGS. 15 and 16. Thus, the eye includes an interiorly tapered surface 134 of anular configuration that incorporates a detent or stop abuttment 135 in the configuration shown. Flapper valve or valve disk 136 is disposed within interior 137 and, at its most innermost position as shown in FIG. 15, will illustrate a closed valve condition with the bulb being returned from the squeezed position to an unsqueezed or normal position. This will be the case where the bulb has just been released and atmospheric pressureis relied upon to thrust the valve disk 136 inwardly. Where the squeeze bulb is manually depressed or squeezed, then the condition shown in FIG. 16 obtains. Thus, the valve tends to advance outwardly, by virtue of the air pressure, in the direction of the arrow so that such air escapes through the anus of the valve across the annular periphery of valve disk 136 and between the same and protruberence 135.

In operation it is seen that valve 120' presents a valve closure that is backed by biasing spring 124 so that aperture 120 is normally closed. When it is desired to evacuate an evacuation chamber of the container as formed by the particular diaphragm used, i.e. whether the chamber is beneath the diagram as in FIG. 2 or above the diagram as shown in FIG. 10, then the bulb 130 is squeezed so as to exhaust air from anus 135, see FIG. 16. This creates the essential absence of air in the passageway at 138 and in the interior region 139 of bulb 130. When the bulb 130 is released as to the applied hand-pressure, then a negative pressure condition exists at 138 and 139, which will operate to open the valve at 120' and allow air to be further exhausted from the interior 140 of the container 116. In this manner the container is exhausted as to internal air.

The depression at 129 is useful for maintaining any absorbent material such as a cotton wad, cylinder or ball, so that any slight chance of moisture entering through and past the valve 120 will be absorbed and hence not passed to the bulb area. This prevents a moisture or contaminating vapors from passing into and out of the bulb 130 proper.

In conclusion, the following points are given special emphasis. Regardless of the type of membrane or diaphragm employed, and whether the negative pressure condition is produced above or below the same, it has been seen that such diaphragm or membrane is effective, with the negative pumping means utilized—and the latter is most important in its own right—to produce a cross-sectional distortion or distension of the diaphragm under the influence of the pumping means and atmospheric pressure which is applied to one side of the diaphragm. Accordingly, the suction created is effective not only to produce a negative pressure area for body fluid recovery, but also for a tensioned diaphragm "pull-down", since temporary imbalance of pressures on opposite sides of the diaphragm exist. As fluid comes in to displace a principal area of the negative pressure area on one side of the diaphragm, then such replacement of the vacuum with liquid effects a lessening of negative pressure at the vacuum area, so that the diaphragm will tend to return to its original condition in its flat, tensioned state. But such action simply causes a prolonged "sucking in" or drawing in of outside fluid over a prolonged time period, under mild conditions, so that the container will tend to fill in a mild, gradually-declining-suction manner, over a prolonged period of time, so as to tend to fill or nearly fill the container. This is much more effective than were the diaphragm eliminated and pressure in the container sharply reduced as even the initial amounts of fluid are drawn in.

The presence of the pumping or pump-down action employed, and particularly the squeeze bulb type of unit used wherein air can be conveniently exhausted, is most important.

The diaphragm or membrane may be designed such that its pull-down as in FIG. 6B will be effective to essentially fill the container above the rising fluid level. In being so designed and relative to proper diaphragm tension and diaphragm, container periphery dimension, the diaphragm can seal off the valves present and even access openings, such that the possibility of the build up of back-pressure and/or dangers of back-flow are eliminated.

The subject structure illustrates that at any time the diaphragm can be pumped back down to the fluid level, wherever it may exist. The patient himself can actuate the pumping mechanism very conveniently, and there is no possibility of forcing fluid back to the patient. The shape of the container can be varied from square to rectangular to round to any other shape, so long as the essential internal diaphragm and associated pumping means are provided.

The invention is very suitable for all types of drainage operations as relates to the human body, including highly useful fluid aspiration structure for gunshot wounds which must be drained under mild-drainage and often field conditions. Springs and valves relating to the squeeze bulb should be weaker or lighter than bulb vacuum; this is preferred rather than specifying specific ounces of collapse in springs. Any outside air introduced during times of emptying is automatically removed from the chamber by the operator when the unit is reactivated.

Present objections to closed-wound units often center in the fact that these require too much hand-pressure to actuate. The subject unit in contrast overcomes such objection by using a pump-down action. Accordingly, rather than relying upon positive pressure production by the pump, a "pumping-down" for producing a vacuum is utilized for accomplishing the results desired. This is most important and quite unique in the art.

Fast emptying is made possible due to the large emptying port shown as at 41 in FIG. 2.

Special note is to be made that an accurate fluid level of vacuum read-out is possible at any time while the unit is either in operation or is deactivated.

Accordingly, what is provided is a new type of negative-pressure pumping device, as shown for example in the various embodiments set forth, for capturing by aspirating drainage fluid from any particular source and especially from the interior body area of a medical patient.

While particular embodiments of the invention have been shown and described, it will be obvious to those skilled in the art the various changes and modifications which may be made without departing from the essential features of the present invention and, therefore, the aim in the appended claims is to cover all such changes and modifications as fall within the true spirit and scope of the invention.

We claim:

1. An aspiration vessel including in combination, a container, resilient elastomeric diaphragm means sealingly engaging and operatively positioned with respect to said container for forming therewith a potential negative-pressure aspiration chamber within said container, said diaphragm having a first side bounding said chamber and an opposite side exposed to atmospheric pressure, said container being provided with an aspiration fluid inlet port communicating with the interior of said chamber, said container being provided with an air passageway communicating with the interior of said chamber, a manually operable pump-down means for reducing the air pressure within said chamber, said pump-down means comprising a conduit member having a pair of branches, one communicating with said air passageway and the other communicating with the atmosphere, said branches having opposed, spring-biased, one-way pressure valves, a squeeze bulb connection communicating with both of said branches, and a squeeze bulb secured to said invention.

2. An aspiration vessel including in combination, a container, resilient elastomeric diaphragm means sealingly engaging and operatively positioned with respect to said container for forming therewith a potential negative-pressure aspiration chamber within said container, said diaphragm having a first side bounding said chamber and an opposite side exposed to atmospheric pressure, said container being provided with an aspiration fluid inlet port communicating with the interior of said chamber, said container being provided with an air passageway communicating with the interior of said chamber, a manually operable pump-down means for reducing the air pressure within said chamber, said pump-down means comprising a one-way valved conduit communicating with said air passageway for receiving air from said chamber, and a pump-down squeeze bulb secured to said conduit and having one-way valve means for exhausting air from said squeeze bulb to the atmosphere.

3. An aspiration vessel including in combination, a container, resilient elastomeric diaphragm means sealingly engaging and operatively positioned with respect to said container for forming therewith a potential negative-pressure aspiration chamber within said container, said diaphragm having a first side bounding said chamber and an opposite side exposed to atmospheric pressure, said container being provided with an aspiration fluid inlet port communicating with the interior of said chamber, said container being provided with a manually operable pump-down means which is in communication with the interior of said chamber for reducing the air pressure within said chamber, and said pump-down means being provided with an absorbent moisture trap.

4. An aspiration vessel including in combination, a container, resilient elastomeric diaphragm means sealingly engaging and operatively positioned with respect to said container for forming therewith a potential negative-pressure aspiration chamber within said container, said diaphragm having a first side bounding said chamber and an opposite side exposed to atmospheric pressure, said container being provided with an aspiration fluid inlet port communicating with the interior of said chamber, said container being provided with a manually operable pump-down means which is in communication with said chamber for reducing the air pressure within said chamber, said diaphragm comprising diaphragm means constructed and dimensioned to seal off the communication between said pump-down mens and said chamber when said diaphragm is in an extended position.

5. An aspiration vessel including, in combination, a container, a cover sealingly secured to and over said container, said cover having a valved fluid inlet port, a flexible fluid collection bag secured to and depending from said cover and surrounding said port, said container having an apertured base, a flexible, resilient, elastomeric diaphragm disposed over said base, and pump-down means secured to said container for producing a negative pressure between said diaphragm and said bag.

6. The combination of claim 5 wherein said fluid inlet port includes valving plunger means, and mechanical operational means for selectively and manually depressing said valving plunger means to open said fluid inlet port.

7. An aspiration vessel adapted to be carried on the body of a patient and to be connected to a wound or the like requiring suction drainage of fluids, said vessel comprising wall means defining a substantially rigid container, a resilient, elastomeric diaphragm in the interior of said container sealingly attached to the walls thereof to provide a chamber from which air can be evacuated, said chamber being defined by said diaphragm and a portion of said walls of said container, an aperture being provided in the portion of the wall means of said container which do not define said chamber, a fluid inlet in the portion of the wall means which define said chamber, said fluid inlet being connected through conduit means to the wound to be drained, an air outlet in the portion of the wall means which define said chamber, manually operable pump-down means including a one-way air inlet valve connected to said air outlet and a one-way air outlet valve communicating with the atmosphere whereby the action of the said pump-down means withdraws air from said chamber to allow atmospheric pressure to extend said diaphragm, the resiliency of the diaphragm providing a continuing negative pressure in said chamber to withdraw fluid from the patient, and as negative pressure is dissipated during drainage of said wound, said manually operable pump-down means may be reactivated to reestablish the directed negative pressure without danger of providing a positive pressure in said chamber which could force fluid material back into the wound being drained.

* * * * *

UNITED STATES PATENT OFFICE
CERTIFICATE OF CORRECTION

Patent No. 4,073,294　　　　　　　　　Dated February 14, 1978

Inventor(s) James Robert Stanley et al

It is certified that error appears in the above-identified patent and that said Letters Patent are hereby corrected as shown below:

Column 7, line 50, "pressureis" should be -- pressure is --

Column 9, line 56, "invention" should be -- connection --

Column 12, line 4, "directed" should be -- desired --.

Signed and Sealed this

Sixth Day of June 1978

[SEAL]

Attest:

RUTH C. MASON
Attesting Officer

DONALD W. BANNER
Commissioner of Patents and Trademarks